United States Patent

Toney et al.

Patent Number: 5,523,433
Date of Patent: Jun. 4, 1996

[54] PROCESS FOR THE PREPARATION OF DIETHYL ESTER DIMETHYL AMMONIUM CHLORIDE

[75] Inventors: Christopher J. Toney, Powell, Ohio; Phillip S. Welte, Janesville, Wis.; Robert K. Lagerman, Grandville, Mich.

[73] Assignee: Witco Corporation, Greenwich, Conn.

[21] Appl. No.: 315,105

[22] Filed: Sep. 29, 1994

[51] Int. Cl.$^6$ .................................................. C07C 99/00
[52] U.S. Cl. ........................ 554/114; 554/103; 554/110; 554/172
[58] Field of Search ................................. 554/103, 114, 554/110, 172

[56] References Cited

U.S. PATENT DOCUMENTS

| | | | |
|---|---|---|---|
| 4,255,484 | 3/1981 | Stevens | 428/286 |
| 4,314,947 | 2/1982 | Hohenschutz et al. | 554/172 |
| 4,339,391 | 7/1982 | Hoffmann et al. | 554/103 |
| 4,789,491 | 12/1988 | Chang et al. | 252/8.75 |
| 4,844,823 | 7/1989 | Jacques et al. | 252/8.8 |
| 5,023,003 | 6/1991 | Yamamura et al. | 252/8.8 |
| 5,093,014 | 3/1992 | Neillie | 252/8.8 |
| 5,126,060 | 6/1992 | Puentes-bravo et al. | 252/8.6 |
| 5,133,885 | 7/1992 | Contor et al. | 252/8.6 |
| 5,180,508 | 1/1993 | Birkhan et al. | 252/8.8 |
| 5,296,622 | 3/1994 | Uphues et al. | 554/110 |

FOREIGN PATENT DOCUMENTS 0309052  3/1989  European Pat. Off. .

*Primary Examiner*—José G. Dees
*Assistant Examiner*—Deborah Carr
*Attorney, Agent, or Firm*—Scully, Scott, Muphy & Presser

[57] ABSTRACT

Disclosed is a process for making di(acyloxyalkyl) di(alkyl) ammonium compounds useful as fabric softeners. The corresponding di(hydroxyalkyl) tertiary amine is diesterified under conditions determined to minimize the formation of monoester side product and then the diester is quaternized under conditions effective to minimize degradation of the quaternized diester.

14 Claims, No Drawings

PROCESS FOR THE PREPARATION OF DIETHYL ESTER DIMETHYL AMMONIUM CHLORIDE

BACKGROUND OF THE INVENTION

The present invention relates to quaternary ammonium compounds useful as fabric softening agents. Such agents are customarily employed in the laundering of fabrics, to impart a feeling of softness and fullness to the fabric, and to reduce the tendency of the fabric to generate static electricity when handled.

Fabric softening agents are often applied to the fabric in the rinse cycle of an automatic clothes washing machine, by adding the agent as part of a pourable liquid or granular solid product. Alternatively, fabric softening agents can be imparted to the fabric in an automatic clothes dryer by placing a thin substrate into the dryer with the fabric, wherein the substrate carries on its surface an effective amount of the fabric softening agent.

The present invention relates more particularly to an improved process in the manufacture of certain quaternary ammonium compounds useful as fabric softening agents. Typically, the manufacture of such agents is a multistep process in which the unquaternized tertiary-substituted amine is prepared, and is then reacted with an appropriate quaternizing agent. The sequence of reactions leading to the formation and recovery of the desired quaternized ammonium compound is notorious for posing problems in obtaining satisfactory yield and conversion rate. The conventional production methods also encounter difficulty in obtaining the desired product with the necessary degree of stability as to the chemical composition, its color and its freedom from unpleasant odor. The existence of such problems is generally believed to be due to the inherently reactive nature of the amine and substituted amine compounds involved, and the relative susceptibility of the reactants employed in the synthesis to undergo competitive side reactions during the synthesis and even following the synthesis leading to the desired end product.

The aforementioned problems are typified in the synthesis of diesterified, dialkylammonium compounds represented by the general formula (1):

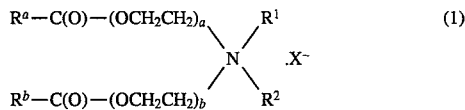

In the aforementioned formula (1), the substituents $R^a$ and $R^b$ are saturated or unsaturated alkyl or alkylene, branched or straight chain, radicals containing 12 to 22 carbon atoms, typically derived from fatty acids which are frequently derived from naturally occurring products such as vegetable or animal sources including tallow. Referring again to formula (1), a and b each represent an integer from 1 to 4, $R^1$ and $R^2$ each represent alkyl containing 1 to 4 carbon atoms, or other substituents such as benzyl, $-CH_2CH_2OH$ or $-CH_2CH(OH)CH_3$. The moiety $X^-$ represents an anion. A preferred example of such compounds is the di(acyloxyethyl) dimethylammonium chlorides, which are disclosed for instance in published European patent application No. 88202037.3. However, the conventionally accepted synthetic route for such compounds, as typified by the synthesis disclosed in the aforementioned European patent application, presents operating difficulties and is unfortunately subject to undesired degradation of the desired final product, leading to off-specification properties such as unacceptable color, aroma, and insufficient active ingredient content. That unattractive synthetic process typically reacts bis(hydroxyalkyl) alkyl tertiary amines with two moles of a long-chain acyl chloride. This procedure suffers from the drawbacks that a highly acidic byproduct is generated which imposes exacting and expensive requirements for its safe recovery, and which byproduct also is believed to interfere with the production of the desired end product. Also, it is difficult to prepare the corresponding monoester in a separate step and then to esterify the remaining hydroxyalkyl group in a subsequent step. This procedure adds further to the complexity of the process, with concomitant reduction of yield and risk of generation of undesired contaminating byproducts in the final desired product.

There is thus a need for an improved process for synthesizing compounds of the aforementioned formula (1) which exhibits improved yield of the desired final product and which makes that product available in a form with enhanced stability and improved purity, i.e., freedom from undesired byproducts and their associated undesired properties.

BRIEF SUMMARY OF THE INVENTION

One aspect of the present invention comprises a process of producing a mixture of compounds of formula (1)

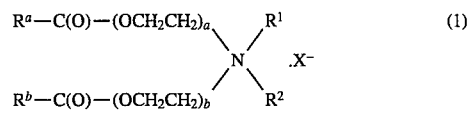

wherein $R^a$ is a saturated or unsaturated alkyl or alkylene radical containing 12 to 22 carbon atoms;

$R^b$ is a saturated or unsaturated alkyl or alkylene radical containing 12 to 22 carbon atoms;

a is 1 to 4;

b is 1 to 4;

$R^1$ is alkyl containing 1 to 4 carbon atoms or benzyl, $-CH_2CH_2OH$ or $-CH_2CH(OH)CH_3$;

$R^2$ is alkyl containing 1 to 4 carbon atoms or benzyl, $-CH_2CH_2OH$ or $-CH_2CH(OH)CH_3$; and $X^-$ is an anion;

comprising the steps of (a) esterifying a mixture of compounds of formula (2)

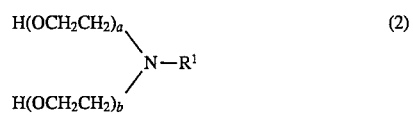

with acids of the formula $R^aCOOH$ and $R^bCOOH$ in the presence of acid having a $pK_a$ below about 5, under conditions effective to form a reaction product comprising a mixture of diesters of formula (3)

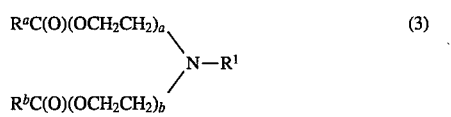

wherein said mixture of compounds of formula (2) contains compounds of formula (2) wherein a and b are 1, and compounds of formula (2) wherein a and b are not 1, in relative amounts such that said mixture of compounds of formula (3) contains about 6 to about 8 wt. % compounds of formula (3) wherein a and b are 1; and continuing said esterification reaction until the acid value of the reaction product is equal to or less than 4.0; and then (b) reacting said diester with a compound of the formula $R^2X$ at a temperature of 180° F. or less, to form a compound of formula (1), in sufficient solvent that the reacting mixture is fluid at the reaction temperature, wherein degradation of the compound of formula (1) is minimized.

This process affords numerous advantages described herein, while avoiding the deleterious effects of synthetic techniques previously employed.

DETAILED DESCRIPTION OF THE INVENTION

Referring to the aforementioned formula (1), $R^a$ and $R^b$ each represent radicals containing 12 to 22 carbon atoms. The corresponding fatty acids $R^aCOOH$ and $R^bCOOH$ can be derived from natural sources or synthetic sources. The fatty acids of the aforementioned structures used in the process of the present invention can be used as purified forms, or as commingled with extraneous source material which does not participate in the reactions that constitute the process of the present invention. Mixtures of compounds having different chain lengths from 12 to 22 carbon atoms long may be employed. In one preferred embodiment, $R^a$ and $R^b$ are derived from the same source and more preferably signify the same radicals.

Referring again to formula (1), the symbols a and b independently represent 1 to 4 and include compounds wherein a and b are each 1, and compounds wherein a and b are each 2, 3 or 4. Preferably, for ease of synthesis and recovery of the desired products, a and b are the same in any given molecule of formula (1).

In formula (1), $R^1$ is straight or branched alkyl containing 1 to 4 carbon atoms, or can also be benzyl, —CH₂CH₂OH or —CH₂CH(OH)CH₃. Preferably, $R^1$ represents lower alkyl and more preferably methyl.

Again referring to formula (1), $R^2$ can be straight or branched alkyl containing 1 to 4 carbon atoms, or can also be benzyl, —CH₂CH₂OH or —CH₂CH(OH)CH₃. Preferably, $R^2$ is methyl or ethyl.

In formula (1) the moiety $X^-$ represents an inorganic or organic anion compatible with the fabric softening properties of the compound of formula (1). Preferred examples of the anion $X^-$ include chloride, bromide, iodide, methyl sulfate, and ethyl sulfate. The more preferred anion is chloride.

The process of the present invention begins with a mixture of precursor compounds of formula (2):

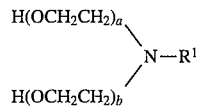
(2)

wherein a, b and $R^1$ are as defined herein. Compounds of formula (2) can readily be obtained or synthesized from known sources.

The compounds of formula (2) are next esterified with fatty acids of the formula $R^aCOOH$ and $R^bCOOH$. The esterification is carried out under carefully prescribed conditions which constitute one aspect of the present discovery.

The esterification can be carried out in a suitable solvent such as xylene, but it is preferred to carry out the esterification in the absence of a solvent. Thus, the fatty acids $R^aCOOH$ and $R^bCOOH$ and the compounds of formula (2) are melted together in a reactor. While the temperature to which this mixture should be raised so as to melt the reactants will vary somewhat with the particular identity of the reactants employed, temperatures on the order of 180°–200° C. are generally satisfactory. The ratio of fatty acids to the compounds of formula (2) should correspond to at least stoichiometric, that is, a mole ratio of at least about 2 moles of fatty acid per mole of the amine of formula (2). Preferred fatty acids include tallow acids, and hydrogenated or partially hydrogenated fatty acids. Also preferred are the mixtures of fatty acids from natural sources such as coconut and rapeseed. Thus, $R^aCOOH$ and $R^bCOOH$ contain 12 to 24 carbon atoms and 0, 1, 2 or 3 carbon-carbon double bonds.

In addition to these reactants, there should be added an amount of a strong acid, preferably one having a $pK_a$ value below about 5. The preferred acid is hypophosphorous acid. As will be more apparent throughout this description, this additional acid component is believed to contribute to the retention of the desired clarity of color, purity, yield, and freedom from degradation of the product. Inorganic acids are preferred. The amount of acid should be up to about 0.5 wt. % of the total amount of reactants present.

Preferably, the inorganic acid is combined with the compounds of formula (2), and the resultant mixture is then reacted with the acids $R^aCOOH$ and $R^bCOOH$. Also, one may if desired add an effective amount of a conventional antioxidant.

The esterification is permitted to proceed essentially to completion. Preferably, the esterification is driven rapidly by the prompt removal of water which is the byproduct of the esterification reaction in a conventional reactor vessel, removal of water can be accomplished by drawing a vacuum over the surface of the liquid reaction mixture, and further assisting the evolution of water by sparging an inert gas such as nitrogen in the reaction mixture. It is preferred that the esterification be carried out such that the water of esterification is removed at a rate effective to minimize the formation of any undesired byproduct.

The esterification should be permitted to proceed under these conditions until the acid value of the reaction mixture reaches or falls below 4.0 and preferably below 2.0. The acid value is defined as the number of milligrams of potassium hydroxide necessary to neutralize the free acids in one gram of the sample. It is determined by direct titration of any free acids by alcoholic KOH after the sample has been dissolved in an appropriate solvent.

$$\text{Acid Value} = \frac{\text{ml KOH} \times N \times 56.1}{\text{sample weight in grams}}$$

The procedure is based on AOCS Method Te 21-64.

The product of the diesterification reaction step is a mixture of compounds of the formula (3):

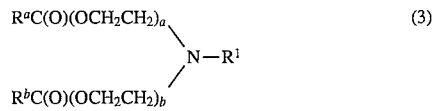
(3)

wherein $R^a$, $R^b$, a, b and $R^1$ have the definitions provided herein. This product can be reacted in the next step of the process of the present invention without intermediate recovery or treatment, although it will often be preferred to transfer the product to a second appropriately equipped reactor, either while maintaining it in the heated, liquified form or after permitting it to solidify in the first reactor.

The mixture of compounds of formula (3) preferably includes 6 wt. % to 8 wt. % of compounds of formula (3) wherein a and b are 1, with the remainder of compounds of formula (3) being characterized with structures wherein a and b are each 2, 3 or 4. Accordingly, the reaction mixture of compounds of formula (2) should include a sufficient amount of compounds of formula (2) wherein a and b are 1, and of compounds of formula (2) wherein a and b are not 1, such that esterification produces the desired distribution of compounds of formula (3).

In the next step of the process of the present invention, the diesters of formula (3) are quaternized under carefully selected conditions. The diesters of formula (3) are reacted with the desired quaternizing agent of the formula $R^2X$, wherein $R^2$ and X have the definitions provided herein. Equimolar amounts of each of these reactants should be employed, although a moderate excess of the quaternizing agent is tolerated. Preferably, the desired amounts of the diesters of formula (3) are dispersed in a suitable liquid solvent in an evacuated reactor. Then, the quaternizing agent is charged to the reactor. Since the reaction of the diesters with the quaternizing agent is exothermic, it is preferable to cool the reactor while the quaternizing agent is being charged to the reactor. However, it subsequently becomes preferable to heat the reaction mixture following introduction of the quaternizing agent, to impart sufficient fluidity to the quaternization reaction mixture to ensure thorough distribution of the quaternizing agent with the diesters. Generally, the pressure within the reactor increases during and after addition of the quaternizing agent.

Preferred quaternizing agents include lower alkyl halides and di(lower alkyl) sulfates, such as methyl chloride, methyl bromide, methyl iodide, dimethyl sulfate and diethylsulfate.

The quaternization reaction mixture should contain a liquid for solvating/dispersing the reactants, in a sufficient amount that the reaction mixture is fluid at temperatures of 180° F. or below, generally at 160° F. to 180° F. If an insufficient amount of solvent is used, it then becomes necessary to raise the temperature of the reaction mixture in order to obtain the desired fluidity. However, quaternizing at a temperature above 180° F. leads to degradation of the color of the desired end product and of the chemical identity of the end product itself. These results render the final product undesirable for further commercial use.

Preferred solvents include ethanol, isopropanol, propylene glycol, butyl carbitol, ethylene glycol and polyethylene glycol. Amounts of the solvent corresponding to about 10–25 wt. % of the entire reaction mixture are generally satisfactory with amounts on the order of about 15 wt. % being preferred.

The quaternization reaction is permitted to proceed until completion. The extent to which the reaction has proceeded can be determined by removing small test portions of the reaction mixture and analyzing to determine the percent of free amine in the sample. Generally, the reaction is considered complete when the free amine content of the reaction mixture is less than 1%. Monitoring the progress of the reaction this way also permits the operator to determine those instances in which an insufficient amount of quaternizing agent has been added, as in such cases the free amine content of the reaction mixture declines to a point beyond which it does not decline further. In such instances, this situation can be remedied simply by introducing additional quaternizing agent into the reactor.

When the free amine content of the reaction mixture has reached the desired level, the reaction mixture is cooled moderately and any excess quaternizing agent is stripped therefrom under vacuum. The quaternizing agent content of the reaction mixture is monitored, and the removal of quarternizing agent is discontinued when the quaternizing agent content reaches a suitable low level, such as less than about 300 ppm. The final product can then be cooled further and recovered from the reactor.

The process of the present invention provides the desired compound of the foregoing formula (1) in advantageously high yield and high purity, and notably free of decomposition of the end product and of discoloration and other evidence that such degradation has occurred.

The process of the present invention is exemplified further in the following illustrative examples.

EXAMPLE

To a reactor equipped with a heating mantle and a stirrer were charged 372.5 pounds of "Distal 51" (a tallow-derived fatty acid mixture having an average molecular weight of 278), and about 350 grams of antioxidant and antifoamer. This mixture was stirred under a vacuum for about 45 minutes and was heated for the final 15 minutes thereof from about 115° F. to about 237° F. A nitrogen sparge was begun. Then about 210 grams of hypophosphorous acid and 89.0 pounds of methyl diethanolamine were added gradually under vacuum over about 15 minutes. A nitrogen blanket (about 15 psia) and stirring were maintained for the next 37 minutes, during which the temperature rose to about 380° F. Nitrogen sparge was then begun again. About 75 minutes later vacuum was reestablished and 35 minutes thereafter another 210 grams of hypophosphorous acid was added. Two hours later heat was discontinued and the vacuum was broken. After 20 minutes of allowing the reaction mixture to cool, the reactor was sealed and 86.4 pounds of ethanol was added, agitation and cooling were continued for 10 minutes, and then the reactor was shut down. The final total amine value of the reaction mixture was 12.9.

Next, the diester formed in the preceding paragraph was placed in a reactor and heated to 170° F. About 52 pounds of methyl chloride was then charged to the reactor to a final reactor pressure of about 90 psia. At the same time, the reactor temperature rose and cooling was applied to maintain the temperature at about 220° F. About 5.25 hours later the reactor was vented and nitrogen sparging was begun. A half hour later vacuum was reestablished, and thereafter sparging was increased. The reactor was shut down about 7.5 hours after the methyl chloride was added. The final product contained about 8.1 wt. % monoester quat and about 76.1 wt % diester quat.

What is claimed is:

1. A process of producing a mixture of compounds of formula (1)

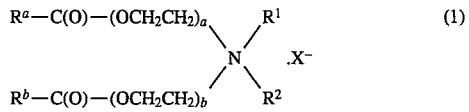

(1)

wherein
  $R^a$ is a saturated or unsaturated alkyl or alkylene radical containing 12 to 22 carbon atoms;
  $R^b$ is a saturated or unsaturated alkyl or alkylene radical containing 12 to 22 carbon atoms;
  a is 1 to 4;
  b is 1 to 4;
  $R^1$ is alkyl containing 1 to 4 carbon atoms or benzyl, —$CH_2CH_2OH$ or —$CH_2CH(OH)CH_3$;

$R^2$ is alkyl containing 1 to 4 carbon atoms or benzyl, —$CH_2CH_2OH$ or —$CH_2CH(OH)CH_3$;

$X^-$ is an anion;

comprising the steps of (a) esterifying a mixture of compounds of formula (2)

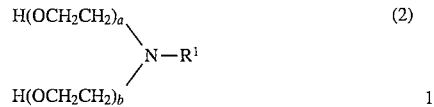

with acids of the formula $R^aCOOH$ and $R^bCOOH$ in the presence of acid having a $pK_a$ below about 5, under conditions effective to form a reaction product comprising a mixture of diesters of formula (3)

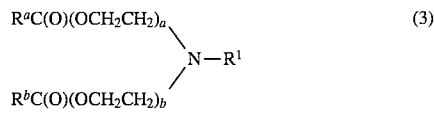

wherein said mixture of compounds of formula (2) contains compounds of formula (2) wherein a and b are 1 and compounds of formula (2) wherein a and b are not 1, in relative amounts such that said mixture of compounds of formula (3) contains about 6 to about 8 wt. % compounds of formula (3) wherein a and b are 1; and continuing said esterification reaction until the acid value of the reaction product is equal to or less than 4.0; and then (b) reacting said diester with a compound of the formula $R^2X$ at a temperature of 180° F. or less, to form a compound of formula (1), in sufficient solvent that the reacting mixture is fluid at the reaction temperature, wherein degradation of the compound of formula (1) is minimized.

2. A process according to claim 1 wherein $R^a$ and $R^b$ are the same.

3. A process according to claim 2 wherein a and b are the same.

4. A process according to claim 3 wherein a and b are 2.

5. A process according to claim 1 wherein a and b are the same.

6. A process according to claim 5 wherein a and b are 2.

7. A process according to claim 1 wherein $R^1$ is ethyl or methyl.

8. A process according to claim 1 wherein said acid having a $pK_a$ below about 5 is hypophosphorous acid.

9. A process according to claim 8 wherein $R^a$ and $R^b$ are the same.

10. A process according to claim 9 wherein a and b are the same.

11. A process according to claim 10 wherein a and b are 2.

12. A process according to claim 8 wherein a and b are the same.

13. A process according to claim 12 wherein a and b are 2.

14. A process according to claim 8 wherein $R^1$ is ethyl or methyl.

* * * * *